United States Patent
Mozdzierz et al.

[11] Patent Number: 6,036,711
[45] Date of Patent: Mar. 14, 2000

[54] REUSABLE CANNULA

[75] Inventors: Patrick D. Mozdzierz, Middletown; Michael M. Ball, Orange, both of Conn.

[73] Assignee: United States Surgical Corporation, Norwalk, Conn.

[21] Appl. No.: 09/025,565

[22] Filed: Feb. 18, 1998

[51] Int. Cl.$^7$ .................................................. A61B 17/34
[52] U.S. Cl. ........................................ 606/185; 604/158
[58] Field of Search .................................. 606/185, 167, 606/207, 170, 174; 604/158, 169, 167, 256; 436/1

[56] References Cited

U.S. PATENT DOCUMENTS

| | | |
|---|---|---|
| 4,067,852 | 1/1978 | Calundann . |
| 4,083,829 | 4/1978 | Calundann et al. . |
| 4,130,545 | 12/1978 | Calundann . |
| 4,161,470 | 7/1979 | Calundann . |
| 4,184,996 | 1/1980 | Calundann . |
| 4,390,668 | 6/1983 | Garver, Sr. . |
| 4,540,737 | 9/1985 | Wissbrun et al. . |
| 4,799,985 | 1/1989 | McMahon et al. . |
| 4,943,280 | 7/1990 | Lander . |
| 4,966,807 | 10/1990 | Harvey et al. . |
| 5,053,016 | 10/1991 | Lander . |
| 5,127,909 | 7/1992 | Shichman . |
| 5,163,327 | 11/1992 | Papai . |
| 5,171,823 | 12/1992 | Charbonneau et al. . |
| 5,203,773 | 4/1993 | Green . |
| 5,330,501 | 7/1994 | Tovey et al. . |
| 5,334,164 | 8/1994 | Guy et al. . |
| 5,336,464 | 8/1994 | Corallo et al. . |
| 5,387,196 | 2/1995 | Green et al. . |
| 5,423,796 | 6/1995 | Shikhman et al. . |
| 5,518,004 | 5/1996 | Schraga . |
| 5,518,927 | 5/1996 | Malchesky et al. ................ 436/1 |
| 5,545,150 | 8/1996 | Danks et al. . |
| 5,549,565 | 8/1996 | Ryan et al. ........................ 604/167 |
| 5,603,702 | 2/1997 | Smith et al. . |
| 5,607,440 | 3/1997 | Danks et al. . |
| 5,893,858 | 4/1999 | Spitz .............................. 606/170 |

OTHER PUBLICATIONS

"Polyesters, Mainchain Aromatic", Encyclopedia of Polymer Science and Engineering, Index vol. pp. 262–279, John Wiley & Sons (1990).

*Primary Examiner*—Michael Buiz
*Assistant Examiner*—Lien Ngo

[57] ABSTRACT

A reusable cannula for use in minimally invasive surgical procedures is fabricated from a material such as a thermotropic liquid crystal polymer (LCP), e.g., a polymer synthesized from p-hydroxybenzoic acid and 6-hydroxy-2-naphthoic acid monomers. The cannula is electrically nonconductive, radiolucent, and experiences an appearance change in response to sterilization by autoclaving. The cannula is fixedly or removably attached to a cannula housing which may have a valve system and/or desufflation port.

14 Claims, 2 Drawing Sheets

REUSABLE CANNULA

BACKGROUND

1. Technical Field

The present disclosure relates to a reusable cannula assembly, and in particular to a cannula assembly which can be used in minimally invasive surgical procedures.

2. Background of Related Art

Cannula assemblies are typically used in minimally invasive surgical procedures such as laparoscopic, endoscopic, and arthroscopic procedures. In minimally invasive procedures the operating instrumentation is typically deployed through a narrow cannula inserted through a small opening or incision in the body to reach an interior operating site. In some procedures, for example, abdominal surgery, the body cavity is insufflated with a biologically non-reactive gas such as $CO_2$. Cannula assemblies are often required to have a seal to prevent egress or entry of fluids from or into the body. Often, the cannula assemblies are provided with a gas port to facilitate desufflation.

From a cost standpoint, it may be desirable to utilize cannula assemblies which can be reused, in whole or in part. Reuse avoids the waste of discarding cannulas and/or cannula assemblies after a single use, but requires cleaning and sterilization of the cannulas or cannula assemblies. Such resterilization is usually done by autoclaving. Autoclaving involves subjecting the object to be sterilized to superheated steam under pressure. To withstand repeated autoclaving, reusable cannulas have typically been fabricated from metals such as stainless steel. However, stainless steel is both electrically conductive and radio-opaque, and generally more expensive than non-metallic cannula.

Accordingly, it is desirable to have a cannula which is electrically non-conducting, radiolucent, and capable of being autoclaved many times, and which is potentially less expensive than a metallic cannula.

SUMMARY

A cannula assembly for use in minimally invasive surgical procedures is provided herein. The cannula assembly includes a reusable cannula fabricated from a thermotropic liquid crystal polymer and defining an axis of the cannula assembly. The cannula assembly also generally includes a cannula housing having first and second openings aligned with the axis of the cannula assembly, the cannula having a proximal end received into the first opening of the cannula housing.

The thermotropic liquid crystal polymer is preferably prepared from p-hydroxybenzoic acid and 6-hydroxy-2-naphthoic acid monomers and is radiolucent and electrically non-conducting. The visible appearance of the cannula advantageously changes in response to the resterilization process, e.g., autoclaving, such appearance change including variations associated with water stains and the like. The cannula housing can include a desufflation port and an interior valve system. The cannula can be fixedly or removably attached to the cannula housing. A chart can be provided with the cannula assembly as components of a kit, the chart containing information which would permit the appearance of the cannula to provide guidance as to whether, and to what degree, the cannula had been sterilized by autoclaving.

BRIEF DESCRIPTION OF THE DRAWINGS

Various embodiments are described herein with reference to the drawings, wherein.

DETAILED DESCRIPTION OF PREFERRED EMBODIMENTS

Figure 1:
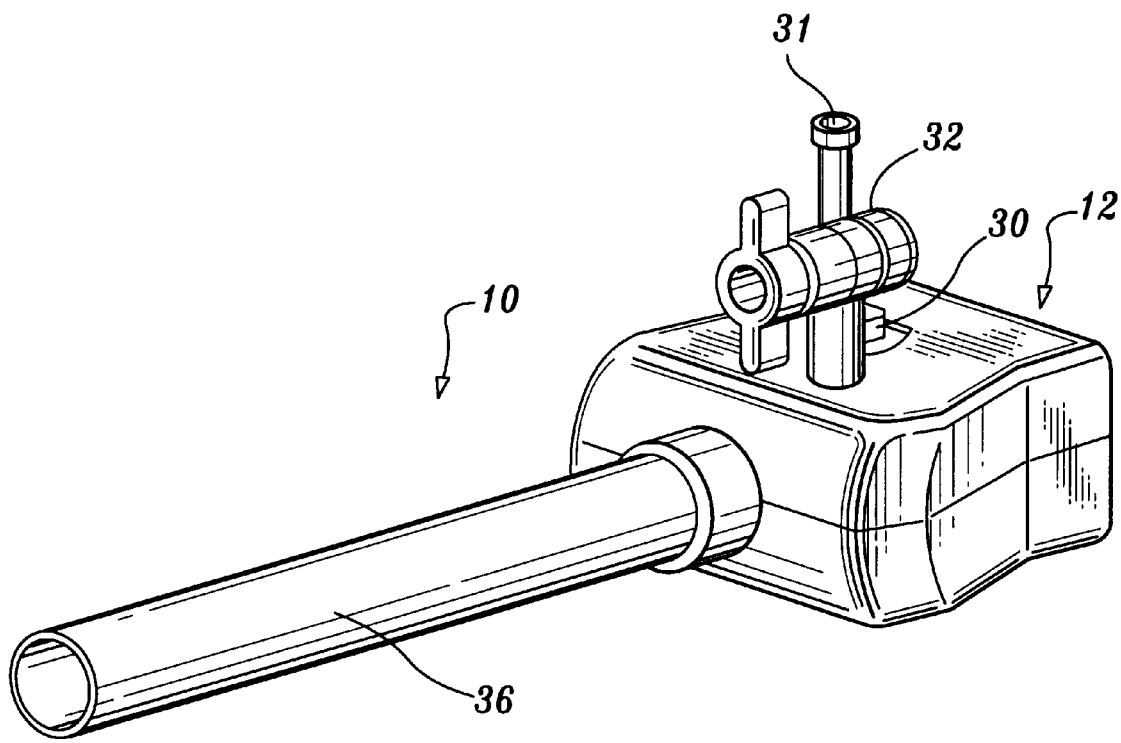
FIG. 1 is a perspective view of a cannula assembly which includes a cannula and a cannula housing.

Referring to FIG. 1, cannula assembly 10 is intended for use in minimally invasive surgical procedures and generally includes a cannula housing 12 optionally having a desufflation gas port 31, a desufflation lever 30 with stopcock valve 32, and a cannula 36 attached thereto. Cannula 36 is an elongated tubular member which is configured and dimensioned so as to permit endoscopic instruments to be inserted therethrough into the body cavity of a patient. Typically, the cannula ranges in diameter from about 3 mm to about 18 mm and can be from about 70 mm to about 150 mm or more in length, these dimensions being given for illustrative purposes only.

Figure 2:
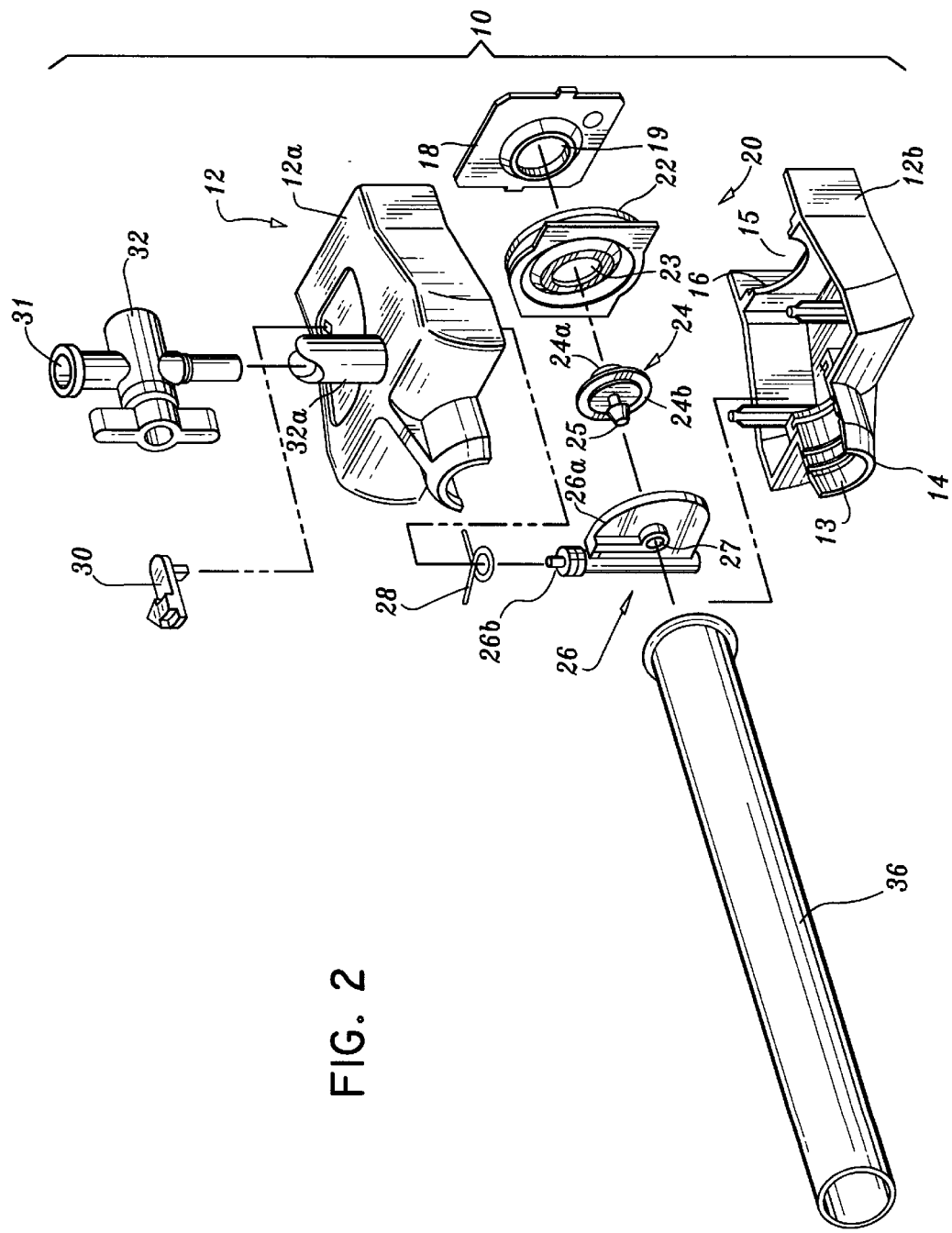
FIG. 2 is an exploded perspective view of a cannula assembly which includes a seal system.

Referring also now to FIG. 2, cannula housing 12 includes top half section 12a and bottom half section 12b suitably attached by ultrasonic welding, adhesives, or the like. However, cannula housing 12 can alternatively be of monolithic construction. Cannula housing 12 optionally encloses a valve system 20, described below, and has at least first and second openings 13 and 15. First opening 13 is defined by flange 14 formed at the distal end of cannula housing 12 and receives the proximal end of cannula 36. Cannula 36 can be permanently secured to cannula housing 12. Preferably, though, cannula 36 is removably attachable to cannula housing 12 by, for example, a screw type threaded engagement or a bayonet type mounting. An example of a detachable engagement is provided in commonly assigned U.S. patent application Ser. No. 08/726,104 filed Oct. 4, 1996, and herein incorporated by reference. Second opening 15 is aligned with first opening 13 and is defined by flange 16 formed at the proximal end of cannula housing 12.

Valve system 20 includes valve seat 22, valve plug 24, valve arm 26 and biasing spring 28. The valve seat 22 is mounted in flange 16 located within the second opening 15 in cannula housing 12. Valve seat 22 defines an aperture 23 extending therethrough which communicates with the first and second openings 13 and 15, respectively, and is positioned in alignment therewith. Valve plug 24 secured to valve arm 26 provides a sealed engagement with aperture 23 in valve seat 22 and includes proximal face 24a, distal face 24b, and stem 25.

The valve arm 26 includes valve plate 26a, aperture 27, and post 26b. Aperture 27 is adapted to receive stem 25 of the valve plug 24. The valve arm 26 is pivotally mounted within cannula housing 12 via post 26b. Biasing spring 28 is positioned on post 26b to bias valve plug 24 toward a position of engagement with valve seat 22 to effect a gas tight seal.

Gas port 31 provides an opening for entry or egress of gas. Gas port 31 includes a stopcock valve 32 and desufflation lever 30. Desufflation lever 30 is provided on cannula housing 12 for manually activating valve arm 26 via post 26b for gas desufflation through the cannula assembly. Stopcock valve 32 is mounted to cannula housing 12 via mounting post 32a to permit selective insufflation or desufflation of the body cavity prior to performing the surgical procedures. Cannula housing 12 may further include a stabilizer plate 18 positioned within or adjacent to the second opening 15 of cannula housing 12, stabilizer plate 18 including a central aperture 19.

A more detailed description of the valve system described herein and its operation may be found in U.S. Pat. No. 4,943,280 to Lander, which is incorporated by reference herein. Alternative valve systems are also contemplated, including those found in commercially available cannula assemblies from the assignee of the present application, e.g., the Versaport™ trocar line.

The cannula 36 of the apparatus described herein is fabricated from an electrically non-conductive thermotropic liquid crystal polymer ("LCP"). Thermotropic LCPs exist in a liquid crystalline state above their melting point, are anisotropic in the melt phase, and are melt processable. Thermotropic LCPs include, but are not limited to, wholly and non-wholly aromatic polyesters, aromatic-aliphatic polyesters, aromatic polyazomethenes, aromatic polyester-carbonates, and wholly aromatic and non-wholly aromatic polyester-amides. A variety of thermotropic LCPs are described in U.S. Pat. Nos. 4,540,737 to Wissbrun et al. and 4,799,985 to McMahon et al., both of which are herein incorporated by reference.

Preferable thermotropic LCPs for use in fabricating cannula 36 include polyesters, in particular, wholly aromatic polyesters. The term "wholly aromatic polyester" as used herein means that the polyester backbone is made of aromatic monomers. Especially useful is a wholly aromatic, thermotropic LCP prepared from p-hydroxybenzoic acid and 6-hydroxy-2-naphthoic acid monomers, commercially available from Celanese Corporation of Somerville, N.J. under the designation VECTRA®. The LCP is preferably heat treated. By "heat treated" is meant that the LCP has been subjected to a melt strength-enhancing process at temperatures near its melting point.

The LCP is radiolucent. That is, it does not cast a shadow in an X-ray image. Moreover, the LCP is resistant to high temperatures. Thus, the cannula may be repeatedly subjected to autoclave sterilization, thereby enabling the cannula to be reused. Autoclave sterilization temperatures can range from about 250° F. to about 300° F., usually about 275° F. The cannula may thus be subjected to scores of autoclave sterilization cycles without loss in product performance. When fabricated from a LCP, such as VECTRA®, or other suitable material, cannula 36 will undergo an appearance change associated with the resterilization process, thereby providing the user with guidance as to whether, and to what degree, the cannula had been autoclave sterilized. The appearance change can be, for example, a change in hue, tint or shade, and/or a staining pattern attributable to water contact. The user may be provided with a kit containing the cannula assembly and a chart with which the cannula can be compared to gauge whether, and to what degree, the cannula assembly has undergone sterilization cycles. If cannula 36 is detachable from the cannula housing 12, cannula 36 can be sterilized while the cannula housing 12 can be discarded.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A cannula assembly for use in minimally invasive surgical procedures, which comprises:
   a reusable cannula fabricated from a thermotropic liquid crystal polymer and defining an axis of the cannula assembly.

2. The cannula assembly of claim 1 further including a cannula housing having first and second openings aligned with the axis of the cannula assembly, the cannula having a proximal end received into the first opening of the cannula housing.

3. The cannula assembly of claim 1 wherein the thermotropic liquid crystal polymer is prepared from p-hydroxybenzoic acid and 6-hydroxy-2-naphthoic acid monomers.

4. The cannula assembly of claim 1 wherein the cannula is radiolucent.

5. The cannula assembly of claim 1 wherein the cannula demonstrates a perceptible appearance change in response to repeated autoclaving of the cannula.

6. The cannula assembly of claim 1 wherein the cannula is electrically non-conducting.

7. The cannula assembly of claim 1 wherein the cannula housing includes a desufflation gas port and an interior valve system.

8. The cannula assembly of claim 1 wherein the cannula is removably attached to the cannula housing.

9. A kit containing:
   a) a cannula assembly for use in minimally invasive surgical procedures, which comprises:
      i) a reusable cannula fabricated from a thermotropic liquid crystal polymer and defining an axis of the cannula assembly, wherein the cannula demonstrates a perceptible appearance change in response to autoclaving process; and,
      ii) a cannula housing having first and second openings aligned with the axis of the cannula assembly, the cannula having a proximal end received into the first opening of the cannula housing; and
   b) a chart containing information as to cannula appearances associated with autoclave sterilization.

10. The cannula assembly of claim 9 wherein the thermotropic liquid crystal polymer is prepared from p-hydroxybenzoic acid and 6-hydroxy-2-naphthoic acid monomers.

11. The cannula assembly of claim 9 wherein the cannula is radiolucent.

12. The cannula assembly of claim 9 wherein the cannula is electrically non-conducting.

13. The cannula assembly of claim 9 wherein the cannula housing includes a desufflation port and an interior valve system.

14. The cannula assembly of claim 9 wherein the cannula is removably attached to the cannula housing.

* * * * *